United States Patent
Sonesson

(10) Patent No.: US 8,501,777 B2
(45) Date of Patent: *Aug. 6, 2013

(54) 3,5-DISUBSTITUTED PHENYL-PIPERIDINES AS MODULATORS OF DOPAMINE NEUROTRANSMISSION

(75) Inventor: Clas Sonesson, Billdal (SE)

(73) Assignee: NSAB, Filial AF Neurosearch Sweden AB, Sverige, Ballerup (DK)

(*) Notice: Subject to any disclaimer, the term of this patent is extended or adjusted under 35 U.S.C. 154(b) by 1136 days.

This patent is subject to a terminal disclaimer.

(21) Appl. No.: 12/089,412

(22) PCT Filed: Oct. 12, 2006

(86) PCT No.: PCT/EP2006/009866
§ 371 (c)(1), (2), (4) Date: Apr. 7, 2008

(87) PCT Pub. No.: WO2007/042295
PCT Pub. Date: Apr. 19, 2007

(65) Prior Publication Data
US 2008/0234321 A1 Sep. 25, 2008

(30) Foreign Application Priority Data
Oct. 13, 2005 (SE) ........................................ 0502254

(51) Int. Cl.
| C07D 211/08 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |

(52) U.S. Cl.
USPC .......................................... 514/317; 546/192

(58) Field of Classification Search
CPC .. C07D 211/08; C07D 401/00; C07D 405/00; C07D 409/00; C07D 411/00; C07D 413/00; C07D 417/00; C07D 419/00; C07D 421/00
USPC ........................................................ 514/317
See application file for complete search history.

(56) References Cited

U.S. PATENT DOCUMENTS

| 3,326,916 | A | 6/1967 | Creighton et al. |
| 3,539,573 | A | 11/1970 | Hunziker et al. |
| 4,202,898 | A | 5/1980 | Depoortere |
| 4,333,942 | A | 6/1982 | Eistetter et al. |
| 4,415,736 | A | 11/1983 | Ciganek et al. |
| 4,504,660 | A | 3/1985 | Klaubert et al. |
| 5,462,947 | A | 10/1995 | Svensson et al. |
| 5,502,050 | A | 3/1996 | Gross |
| 6,175,015 | B1 | 1/2001 | Yuan et al. |
| 6,924,374 | B2 * | 8/2005 | Sonesson et al. ............. 546/192 |
| RE41,315 | E * | 5/2010 | Sonesson et al. ............. 546/192 |
| 7,763,639 | B2 * | 7/2010 | Sonesson et al. ............. 514/317 |
| 2003/0004169 | A1 * | 1/2003 | Sonesson et al. ........ 514/252.13 |
| 2003/0109532 | A1 | 6/2003 | Sonesson et al. |
| 2007/0032469 | A1 | 2/2007 | Isaac et al. |
| 2007/0149542 | A1 | 6/2007 | Sonesson et al. |
| 2007/0238878 | A1 * | 10/2007 | Desmond et al. ............. 546/232 |

FOREIGN PATENT DOCUMENTS

| EP | 0 060 179 A1 | 9/1982 |
| EP | 0 094 159 B1 | 11/1983 |
| EP | 0 369 887 A2 | 5/1990 |
| EP | 0 533 266 A1 | 3/1993 |
| EP | 0 533 267 A1 | 3/1993 |
| EP | 0 533 268 A1 | 3/1993 |
| EP | 0 659 743 A1 | 12/1993 |
| EP | 0 675 118 A2 | 10/1995 |
| FR | 1.459.013 | 4/1966 |
| GB | 850662 | 10/1960 |
| GB | 1 464 525 | 2/1977 |
| GB | 1 560 271 | 2/1980 |
| GB | 2 027 703 A | 2/1980 |
| GB | 2 078 746 A | 1/1982 |
| GB | 2 083 476 A | 3/1982 |

(Continued)

OTHER PUBLICATIONS

Manoury P. M. et al., "Synthesis and Analgesic Activities of Some (4-Substituted phenyl-1-piperazinyl)alkyl 2-Aminobenzoates and 2-Aminonicotinates", J. Med. Chem. 1979 22 (5) 554-559.

Morita S. et al., "Practical Application of the Palladium-catalyzed Amination in Phenylpiperazine Synthesis: An Efficient Synthesis of a Metabolite of the Antipsychotic Agent Aripiprazole", Tetrahedron 1998 54 (19) 4811-4818, May 1, 1998.

Yasuo Oshiro et al., "Novel Antipsychotic Agents with Dopamine Autoreceptor Agonist Properties: Synthesis and Pharmacology of 7-[4-(4-Phenyl-1-piperazinyl)butoxy]-3,4-dihydro-2(1H)-quinolinone Derivatives", J. Med. Chem. 1998 41 (5) 658-667, (1998).

(Continued)

*Primary Examiner* — Rita Desai
*Assistant Examiner* — Ben S Michelson
(74) *Attorney, Agent, or Firm* — Birch, Stewart, Kolasch & Birch, LLP

(57) ABSTRACT

The present invention relates to compounds having therapeutic effects against disorders in the central nervous system, and in particular substituted phenylpiperidines of the formula 1:

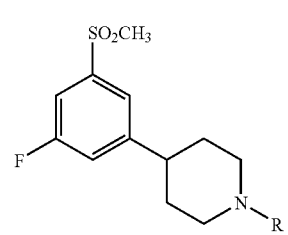

(1)

wherein R is as defined herein.

2 Claims, No Drawings

(56) References Cited

FOREIGN PATENT DOCUMENTS

| | | |
|---|---|---|
| JP | 2000-86603 A | 3/2000 |
| NL | 6510107 | 2/1966 |
| WO | WO-89/05799 A1 | 6/1989 |
| WO | WO-91/09594 A1 | 7/1991 |
| WO | WO-92/18475 A2 | 10/1992 |
| WO | WO-93/00313 A2 | 1/1993 |
| WO | WO-93/04684 A1 | 3/1993 |
| WO | WO 95/33729 | 12/1995 |
| WO | WO-97/03986 A1 | 2/1997 |
| WO | WO-98/11068 A1 | 3/1998 |
| WO | WO 98/56787 | 12/1998 |
| WO | WO-00/03713 A1 | 1/2000 |
| WO | WO-00/78728 A1 | 12/2000 |
| WO | WO-01/46144 A1 | 6/2001 |
| WO | WO-01/46145 A1 | 6/2001 |
| WO | WO-01/46146 A1 | 6/2001 |
| WO | WO-0146146 A | 6/2001 |
| WO | WO-02/05819 A1 | 1/2002 |
| WO | WO-02/059108 A1 | 8/2002 |
| WO | WO-2004/099150 A2 | 11/2004 |
| WO | WO-2005/019215 A1 | 3/2005 |
| WO | WO-2005/121087 A1 | 12/2005 |
| WO | WO-2005/121088 A1 | 12/2005 |
| WO | WO-2005/121092 A1 | 12/2005 |
| WO | WO-2006/039325 A2 | 4/2006 |
| WO | WO-2006/040156 A1 | 4/2006 |
| WO | WO 2006040156 A1 * | 4/2006 |
| WO | WO-2007/065655 A1 | 6/2007 |

OTHER PUBLICATIONS

Smaill et al., "Mono- and difunctional nitrogen mustard analogues of the DNA minor groove binder pibenzimol. Synthesis, cytotoxicity and interaction with DNA", Anti-Cancer Drug Design 1998 13 (3) 221-242.

Beugelmans et al., "Synthese of 5- and 6-membered heterocycles by a strategy combining SNAr and SRN1 reactions", Bulletin de la Societe Chimigue de France 1995 132 (3) 306-313.

Egawa et al., "A New Synthesis of /H-Pyrido[1,2,3-de][1,4]benzoxazine Derivatives including an Antibacterial Agent, Ofloxacin", Chemical & Pharmaceutical Bulletin 1986 34 (10) 4098-4102.

Takai et al., "Reaction of Spiro[4H-3, 1-benzoxazine-4,4'-piperidin]-2(1H)-one Derivatives and Related Compounds with Phosphorus Oxychioride", Chemical Pharmaceutical Bulletin 1986 34 (5) 1901-1906.

Zhang et al., "Studies on antimalarials. III. Synthesis and antimalarial effects of some derivatives of 2,4-diamino-6-substituted piperazinylguinazolines", Yaoxue Xuebao 1981 16 (6) 415-424.

Klaubert et al., "N-(Aminophenyl) oxamic Acids and Esters as Potent, Orally Active Antiallergy Agents", Journal of Medicinal Chemistry 1981 24 (6) 742-748.

Self et al, "Cine and tele Substitutions in the Reaction of 2,3-Dinitroaniline with Secondary Amines", Journal of the Chemical Society, Chemical Communications 1980 (6) 281-282.

Elslager et al., "Folate Antagonists. 3. 2,4-Diamino-6-(heterocyclic)guinazolines, a Novel Class of Antimetabolites with Potent Antimalarial and Antibacterial Activity", Journal of Medicinal Chemistry 1972 15 (8) 827-836.

Berberian et al., "Comparison of Schistosomicidal Activity of Xanthenones and 4-Methyl-3-chloroanilines and Their Hydroxymethyl Analogs in Swiss Mice and Syrian Hamsters Infected with *Schistosoma mansoni*", Journal of Medicinal Chemistry 1969 12 (4) 607-610.

David W. Henry "A Facile Synthesis of Piperazines from Primary Amines (1)" Journal of Heterocyclic Chemistry 1966 3 (4) 503-511.

Bergel et al., "Synthetic Analesics. Part I. Synthesis of Basic Benzofuran Derivatives and certain 4-Phenylpiperidine Compounds", J. Chem. Soc. 1944 261-264.

Nacci el al., "Antiblastic substances. LII. Tylophorine analogs. 1. Synthesis and cytostotic and cytotoxic activity of 4-(3,4-dimethoxphenyl)piperidine", Farmaco Ed. Scintifica 1972 328 (5) 399-410.

Sonesson et al., "Substituted (S)-Phenylpiperidines and Rigid Congeners as Preferential Dopamine Autoreceptor Antagonists: Synthesis and Structure-Activity Relationships", Journal of Medicinal Chemistry 1994 37 (17) 2735-2753.

Rádl et al., "Synthesis of Piperidine Analogs of 1-(3-Chlorophenyl)piperazine, a Well Known Serotonin Ligand", Journal of Heterocyclic Chemistry 1999 36 (4) 1017-1022.

Altomare et al., "Quantitative Structure-Metabolism Relationship Analyses of MAO-Mediated Toxication of 1-Methyl-4-phenyl-1,2,3,6-tetrahydropyridine and Analogues", Chemical Research in Toxicology 1992 5 (3) 366-375.

Roth et al., "Biochemical Pharmacology of Midbrain Dopamine Neurons", Psychopharmacology: The Fourth Generation of Progress, Raven Press Ltd., New York 1995, Bloom et al., Chapter 21, pp. 227, 237.

Moore et al., "Dopaminergic Neuronal Systems in the Hypothalamus", Psychopharmacology: The Fourth Generation of Progress, Raven Press Ltd., New York 1995, Bloom et al., Chapter 22, pp. 245, 254.

Michel Le Moal, "Mesocorticolimbic Dopaminergic Neurons", Functional and Regulatory Roles, Psychopharmacology: The Fourth Generation of Progress, Raven Press Ltd., New York 1995, Bloom et al., Chapter 25, pp. 283, 292.

Philip Seeman, "Dopamine Receptors", Clinical Correlates, Psychopharmacology: The Fourth Generation of Progress, Raven Press Ltd., New York 1995, Bloom et al., Chapter 26, pp. 295-301.

"Psychopharmacology of Sexual Behavior", Psychopharmacology: The Fourth Generation of Progress, Raven Press Ltd., New York 1995, Bloom et al., pp. 744-746.

George F. Koob, "Animal Models of Drug Addiction", Psychopharmacology: The Fourth Generation of Progress, Raven Press Ltdl., New York 1995, Bloom et al., Chapter 66, pp. 759-760.

Geyer et al., "Animal Models of Psychiatric Disorders", Psychopharmacology: The Fourth Generation of Progress, Raven Press Ltd., New York 1995, Bloom et al., Chapter 68, pp. 787, 793-795.

Paul Wiliner, "Dopaminergic Mechanisms in Depression and Mania", Psychopharmacology: The Fourth Generation of Progress, Raven Press Ltd., New York 1995, Bloom et al., Chapter 80, pp. 921-925, 927-928.

Bunney et al., "Schizophrenia and Glutamate", Psychopharmacology: The Fourth Generation of Progress, Raven Press Ltd., New York 1995, Bloom et al., Chapter 101, pp. 1205, 1207-1209.

Price et al., "Pharmacological Challenges in Anxiety Disorders", Psychopharmacology: The Fourth Generation of Progress, Raven Press Ltd., New York 1995, Bloom et al., Chapter 111, pp. 1311, 1317, 1318, 1320.

Amos D. Korczyn, "Parkinson's Disease", Psychopharmacology: The Fourth Generation of Progress, Raven Press Ltd., New York 1995, Bloom et al., Chapter 126, pp. 1479-1482.

George A. Bray, "Obesity, Fat Intake, and Chronic Disease", Psychopharmacology: The Fourth Generation of Progress, Raven Press Ltd., New York 1995, Bloom et al., Chapter 137, pp. 1591, 1600.

Katherine A. Halmi, "Basic Biological Overview of Eating Disorders", Psychopharmacology: The Fourth Generation of Progress, Raven Press Ltd., New York 1995, Bloom et al., Chapter 138, pp. 1609-1610, 1612.

"Pathophysiology of Tobacco Dependence", Psychopharmacology: The Fourth Generation of Progress, Raven Press Ltd., New York 1995, Bloom et al., p. 1725.

Carlsson et al., "Interactions between glutamatergic and monoaminergic systems within the basal ganglia-implications for schizophrenia and Parkinson's disease", TINS 1990 13 (/) 2/2-2/6.

Coyle et al., "Alzheimer's Disease: A Disorder of Cortical Cholinergic Innervation", Science 1983 219 1184-1190.

Feldman et al., "Mind-Altering Drugs", Principles of neuropsychopharmacology, Chapter 17, 1997 731 762-763.

Grünblatt et al., "Potent neuroprotective and antioxidant activity of apomorphine in MPTP and 6-hydroxydopamine induced neurotoxicity", J Neural Transm (1999) [Suppl] 55: 57-70.

Grünblatt et al., "Neuroprotective Strategies in Parkinson's Disease Using the Models of 6-Hydroxydopamine and MPTPα", pp. 262-263, (2000).

Philip G. Strange, "Antipsychotic Drugs: Importance of Dopamine Receptors for Mechanisms of Therapeutic Actions and Side Effects", Pharmacol. Rev. 2001 53 (1) 119-133.

Wolff, Manfred E. Burger's Medicinal Chemistry—4th Edition, Part III; John Wiley & Sons 1979 872-873.

* cited by examiner

3,5-DISUBSTITUTED PHENYL-PIPERIDINES AS MODULATORS OF DOPAMINE NEUROTRANSMISSION

FIELD OF THE INVENTION

The present invention relates to new modulators of dopamine neurotransmission, and more specifically to new disubstituted phenyl-piperidines, and use thereof.

BACKGROUND OF THE INVENTION

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly, at central dopamine receptors are commonly used in the treatment of neurological and psychiatric disorders, e.g. Parkinson's disease and schizophrenia. However, currently available dopaminergic pharmaceuticals may have severe side effects. For instance, dopamine antagonists are known to induce both motor (extrapyramidal side effects; EPS) and mental side effects (e.g. anhedonia, dysphoria, and impairment of cognition), and dopaminergic agonists are known to induce dyskinesias and psychoses (Goodman and Gilman's the Pharmacological Basis of Therapeutics, 9th ed./McGraw-Hill, USA. Chapter 18, p 407-416, Chapter 22, p 509-512, p 515-516).

An approach adopted by many researchers to improve efficacy and reduce side effects of dopaminergic pharmaceuticals, is to develop novel dopamine receptor ligands with selectivity at specific dopamine receptor subtypes or with regional selectivity. Yet another class of compounds acting through the dopamine systems of the brain are dopaminergic stabilizers, which have shown to be useful in the treatment of both neurologic and psychiatric disorders (A. Ekesbo, PhD Thesis, Uppsala University, Sweden: Functional consequences of dopaminergic degeneration; clinical and experimental studies using a novel stabilizer of dopaminergic systems: Ekesbo et al, (–)-OSU6162 inhibits levodopa-induced dyskinesias in a monkey model of Parkinson's disease, *Neuroreport,* 8, 2567, 1997; Tedroff et al. Long-lasting improvement in motor function following (–)-OSU6162 in a patient with Huntington's disease. *Neurology,* 22; 53:1605-6, 1999; Gefvert O. et al, (–)-OSU6162 induces a rapid onset of antipsychotic effect after a single dose. A double-blind placebo-controlled pilot study. *Scandinavian Society for Psychopharmacology,* 41$^{st}$ Annual Meeting, Copenhagen Denmark Nordic Journal of Psychiatry 54/2 93-94, April 2000: Carlsson et al, *Annu. Rev. Pharmacol. Toxicol.,* 41, 237, 2001; Carlsson et al. *Current Medicinal Chemistry,* 11, 267, 2004).

Another dopaminergic compound, which has been referred to as a dopamine-serotonin system stabiliser, as well as a partial DA $D_2$ receptor agonist, is the recently launched antipsychotic compound aripiprazole (Burris et al, *Pharm. Exp. Ther, vol.* 302, 381, 2002.). Furthermore, compounds referred to as dopaminergic stabilizers have been described in WO01/46145, WO01/46146, Pettersson et al. The development of ACR16. A new class of dopaminergic stabilizers. *Society for Neuroscience* 32$^{nd}$ *Annual Meeting, Abstract* 2002, Vol. 28 part 1 1028, Orlando USA 2002; and Nyberg et al Efficacy and tolerability of the new dopamine stabiliser ACR16 a randomised placebo-controlled add-on study in patients with schizophrenia 12th BIENNIAL WINTER WORKSHOP ON SCHIZOPHRENIA, 7-13 Feb. 2004, Davos, Switzerland.

The typical pharmacological effects that are characteristic for dopaminergic stabilizers as described in WO01/46145, WO01/46146 and Pettersson et al. 2002 can be summarized as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimietic compounds in the rat. In the present invention this is referred to as a dopaminergic stabilizer profile.

It is known that certain pharmaceutically active compounds which are used in the treatment of neurological and psychiatric disorders (especially antipsychotic and antidepressant compounds) may have undesirable effects on those cardiac potassium channels which are involved in the electric repolarisation of cardiac cells, commonly referred to as hERG channels (human ether-a-go-go related gene encoded voltage-de-pendent potassium channel) or $I_{Kr}$ (rapidly activating delayed rectifier potassium current) channels. Drugs which block these channels can induce ventricular arrhythmia (Torsade de Pointes, TdP), leading to sudden death in otherwise healthy subjects. Indication that a drug might have undesirable effects on cardiac repolarisation is seen through prolongation of the QT interval of the electrocardiogram, which is considered to be a surrogate marker for risk of TdP. A number of drugs have been withdrawn from the market due to unacceptable side effects relating to cardiac arrhythmia (I. Cardiovasc. Electrophysiol. 15, 475, 2004; Eur. J. Pharm., 450, 37, 2002; Cardiovascular Research, 58, 32, 2003)

This invention relates to the field of treatment of mammals suffering from CNS disorders in which the symptoms can be affected by dopaminergic functions, where the treatment comprises administering to said mammal an amount of a new type of compound, with a dopaminergic stabilizer profile. In addition, the compounds display low affinity at cardiac potassium channels, reducing the risk of serious cardiac side effects.

DESCRIPTION OF PRIOR ART

Compounds belonging to the class of substituted 4-(phenyl)-N-alkyl-piperidines have been previously reported. Among these compounds, some are inactive in the CNS, some display serotonergic or mixed serotonergic/dopaminergic pharmacological profiles while some are full or partial dopamine receptor agonists or antagonists with high affinity for dopamine receptors.

A number of 4-phenylpiperidine derivatives are known. EP0369887 disclose substituted 4-(meta-trifluoromethylphenyl)-1,2,3,6-tetrahydropyridines for treatment of anxiety.

WO00/03713 discloses a method for the treatment of schizophrenia and other dopamine system dysfunctions by using substituted 1-methyl-4-phenyl-1,2,3,6-tetrahydropyridines.

Glennon et al. (U.S. Pat. No. 6,057,371) claim a method for treating sigma receptor associated CNS disorder, comprising the administration of arylamines, including arylpiperidines, which are either unsubstituted or mono-substituted at the aryl ring. The compounds exhibit a high binding affinity with respect to the sigma receptor. WO 91/095954 states that the term "high affinity" is intended to mean a compound which exhibits an $IC_{50}$ of less than 100 nM in the assay against $^3$H-DTG described in Weber et al. Proc. Natl. Acad. Sci. (USA) 83: 8784-8788). Specifically, WO 91/095954 discloses compositions relating to "the discovery that certain phenylalkyl-amine, aminotetraline, piperazine, piperidine and related derivatives have high binding to the sigma receptor and unexpectedly low binding for the PCP and DA receptors" (see page 11, lines 33-36).

WO 91/095954 and WO 93/00313 both require that the compounds have a high binding affinity to the sigma receptor and do not disclose that the compounds are pharmacologically active in the absence of sigma receptor affinity. In addition, clinical studies investigating the properties of sigma receptor ligands in schizophrenic patients have not generated evidence of antipsychotic activity, nor activity in any other CNS disorder. Two of the most extensively studied selective sigma receptor antagonists, BW234U (Rimcazole) and BMY14802, have both failed in clinical studies in schizophrenic patients (Borison et al, 1991, *Psychopharmacol Bull* 27(2): 103-106; Gewirtz et al, 1994, *Neuropsychopharmacology* 10:37-40).

WO97/23216 discloses 4-substituted piperidine analogues with the formula:

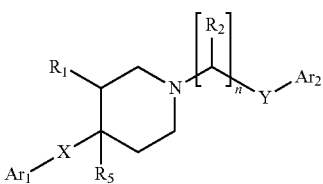

in which R5 may be selected from OH, and Ar1 may be substituted. Such compounds are used for treating CNS trauma, psychosis and neurodegenerative disorders, among others, through selective blockade of NMDA receptor subtypes.

U.S. Pat. No. 4,485,109 discloses compounds with formula:

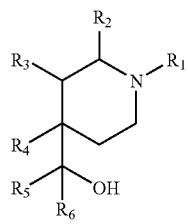

which are used as psychotherapeutic agents, particularly as antidepressants.

EP 1177792 discloses, among others, compounds with the structure:

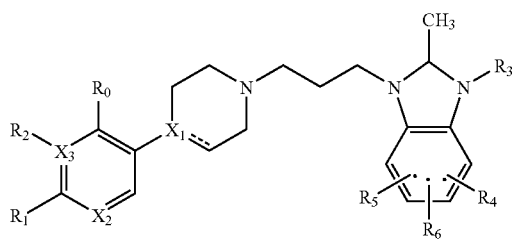

having dopaminergic activity—particularly as D4 receptor ligands—and useful for the treatment of novelty-seeking disorders.

WO98/51668 discloses substituted piperidine derivatives of the formula:

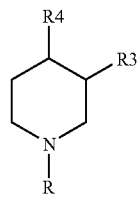

which possess properties as monoamine neurotransmitter i.e. dopamine, serotonin, noradrenaline, reuptake inhibitors. The compounds are said to be useful in the treatment of Parkinsonism, depression, pseudodementia, obesity, narcolepsy, drug addiction, and/or abuse, attention-deficit hyperactivity disorders, senile dementia or memory dysfunctions.

In addition, it is known that compounds with formulae II (WO01/46145) and III (WO01/46146) possess dopaminergic stabilizer properties.

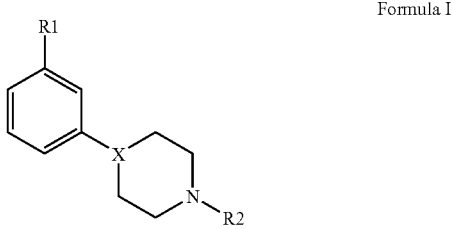

Formula I

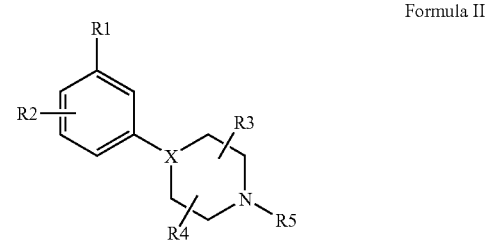

Formula II

In formula I;
X is, inter alia, CH, $R_1$ is selected from the group consisting of $OSO_2CF_3$, $OSO_2CH_3$, $SOR_3$, $SO_2R_3$, $COR_3$, $CN$, $NO_2$, $CONHR_3$, $CF_3$ (proviso X is CH or C) F, Cl, Br, I (wherein $R_3$ is as specified below);
$R_2$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_4$ (wherein $R_4$ is as specified below);
$R_3$ is selected from the group consisting of $C_1$-$C_3$ alkyl, $CF_3$, or $N(R_2)_2$;
$R_4$ is selected from the group consisting of $C_3$-$C_6$ cycloalkyl, 2-tetrahydrofurane, 3-tetrahydrofuran.
In formula II;
X is, inter alia, CH, $R_1$ is selected from the group consisting of $OSO_2CF_3$, $OSO_2CH_3$, $SOR_7$, $SO_2R_7$, $COR_7$, $CN$, $NO_2$, $CONHR_3$, $CF_3$, F, Cl, Br, I (wherein $R_3$ is as specified below), 3-thiophene, 2-thiophene, 3-furane, 2-furane;
$R_2$ is selected from the group consisting of F, Cl, Br, I, CN, $CF_3$, $CH_3$, $OCH_3$, $OH$, $NH_2$
$R_3$ and $R_4$ are independently H or $C_1$-$C_4$ alkyl
R5 is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_6$;

$R_6$ is selected from the group consisting of $C_3$-$C_6$ cycloalkyl, 2-tetrahydrofurane, 3-tetra-hydrofuran.

$R_7$ is selected from the group consisting of $C_1$-$C_3$ alkyl, $CF_3$ or $N(R_4)_2$ However, neither WO01/46145 (Formula I) nor WO01/46146 (Formula II) disclose pharmacology data for the 3,5 disubstitution in the phenyl ring disclosed in the present invention. The following structure is known as an synthesis example in WO01/46146 (Example 44 4-[3-fluoro-5-(trifluoromethyl)phenyl-]1-propylpiperidine).

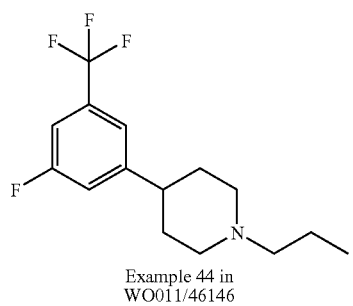 [SMILES: CCCN1CCC(c2cc(F)cc(C(F)(F)F)c2)CC1]

Example 44 in
WO011/46146

In addition, there is no guidance in neither WO01/46145 (Formula I) nor WO01/46146 (Formula II) how to obtain potent dopaminergic stabilisers.

There remains a need for new pharmaceutically active compounds, especially useful in treatment of disorders in the central nervous system, having increased potency as dopaminergic stabilisers. It is also desirable that any such pharmaceutically active compound has reduced propensity for side effects, particularly as regards cardiac arrhythmia.

SUMMARY OF THE INVENTION

The object of the present invention is to provide new pharmaceutically active compounds, especially useful in treatment of disorders in the central nervous system, having increased potency as dopaminergic stabilisers (See Table 1, column 1) with a low propensity to block the hERG channel (see Table 1, column 2). These compounds have particular advantages with respect to reduced side effects, particularly cardiac side effects.

The 3,5-disubstitution in the present invention surprisingly improves the potency and efficacy compared to alternative substitution patterns (e.g. 3,4-disubstitution in which the 4-position is halogen) or mono substituted (3-position). In addition the compounds of the present invention displays lower affinity for the hERG channel compared to compounds from prior art.

The substances according to the present invention have been biologically tested in the rat where they have been found to act preferentially on dopaminergic systems in the brain. They have effects on biochemical indices in the brain with the characteristic features of dopamine antagonists. However, the substances according to the invention show no inhibitory effects on spontaneous locomotion over a wide dose range. Further, the substances according to the invention can induce a slight behavioural activation, in particular when baseline locomotor activity is low. However, the substances in the present invention inhibit the behavioural activation induced by psychostimulants and psychotomimetics.

The substances according to the present invention display low potency at inhibiting the hERG channel, as measured by IC50 in a Rapid ICE assay (for details see experimental section), indicating a low risk for QT interval prolongation and arrhythmia in man.

DETAILED DESCRIPTION OF THE INVENTION

The present invention relates to new piperidines in the form of free base or pharmaceutically acceptable salts thereof, pharmaceutical compositions containing said compounds and use of said compounds in the manufacture of pharmaceuticals being dopamine neurotransmitters and therapy.

More precisely, the present invention relates to piperidine compounds of Formula 1:

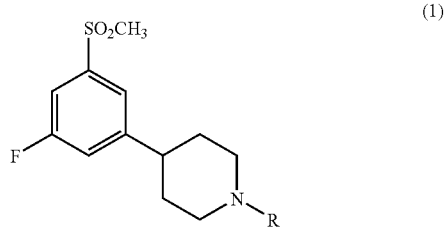

(1)

wherein R is selected from the group consisting of $C_1$-$C_3$ alkyls and allyl;

and pharmaceutically acceptable salts thereof.

In particular embodiments R is selected from the group consisting of n-propyl and ethyl.

A further aspect of the invention relates to a method for treating central nervous system disorders by administering a therapeutically active amount of the compounds of formula 1 or a pharmaceutically acceptable salt thereof to a mammal, including human, suffering from a central nervous system disorder. Additionally, the present invention relates to a method for treating any disorders listed herein, by administering a therapeutically active amount of the compounds of formula 1 or a pharmaceutically acceptable salt thereof to a mammal, including human, suffering from said disorder.

Inclusion of two substituents on the aryl ring of such compounds—one in the 3-position (meta 1) and the other in the 5-position (meta 2)—increases their potency in modulating dopamine neurotransmission. The unprecedented increase in potency of these 3,5-disubstituted compounds as compared to the mono-substituted, or the 3,4-disubstituted compounds is illustrated in TABLE 1.

In addition, the 3,5 disubstitution in the present invention is found to decrease side effects relating to cardiac arrhythmia, as measured by the effect of these compounds on the hERG potassium channel (Rapid Ice). The unprecedented reduction in side effects of such substituted compounds is illustrated in TABLE 1.

TABLE 1

Effects of compounds in the present invention on reduction of amphetamine-induced hyper-locomotion (estimated $ED_{50}$ values) and affinity for the hERG ion channel (IC50 values). Comparative examples from prior art is also included. For methods and statistical calculations see the enclosed tests.

| | ED50 amf* μmol/kg | Rapid ICE (IC50, nM) |
|---|---|---|
| Comparative examples | | |
| 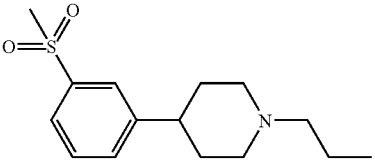 Example 6 of WO01/46145 | 52 | Not tested |
| 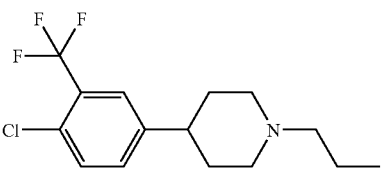 Example 9 of WO01/46146 | 34 | 610 |
| 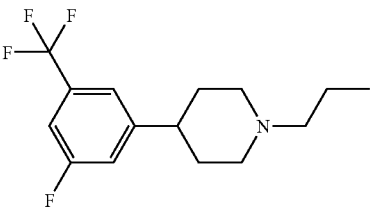 Example 44 in WO01/46146 | 14 | 1500 |
| Examples | | |
| 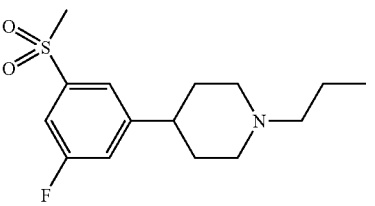 Example 1 | 12 | 9800 |
| 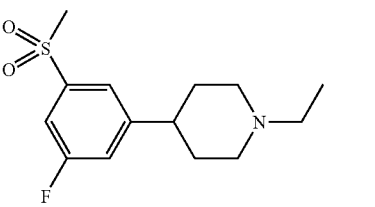 Example 2 | 28 | 21670 |

*Effects of compounds in the present invention on reduction of amphetamine-induced hyper-locomotion. Comparative examples from prior art is also included. For methods and statistical calculations see the enclosed tests.

An important observation is that the presence of the F and $SO_2CH_3$ substituents in the meta 1 and meta 2 positions in the phenyl ring improve the efficacy and potency of the dopaminergic stabilizer compared to the mono or 3,4 disubstitution (e.g. Example 6 of WO01/46145 and Example 9 of WO01/46146), but also reduces the affinity for the hERG channel. Such an outcome would not have been predicted as a general rule One aim of the present invention is to provide new compounds for therapeutic use, and more precisely compounds for modulation of dopaminergic systems in the mammalian brain, including human brain. Preferably such compounds have lowered side-effects with respect to cardiac potassium channel inhibition.

Another aim of the invention is to provide compounds with therapeutic effects after oral administration.

The preferred substituted structures are
1-ethyl-4-[3-fluoro-5-(methylsulfonyl)phenyl]piperidine
4-[3-fluoro-5-(methylsulfonyl)phenyl]-1-propylpiperidine
1-allyl-4-[3-fluoro-5-(methylsulfonyl)phenyl]piperidine The compounds and compositions according to the present invention possess dopamine-modulating properties and are useful in treating numerous central nervous system disorders, including both psychiatric and neurological disorders. Particularly, the compounds and their pharmaceutical compositions may be used in the treatment of CNS disorders where the dopaminergic system is dysfunctional due to direct or indirect causes.

The compounds and compositions according to the invention can be used to improve all forms of psychosis, including schizophrenia and schizophreniform disorders as well as drug induced psychotic disorders and bipolar disorder. They can also be used in the treatment of a condition selected from the group consisting of iatrogenic and non-iatrogenic psychoses and hallucinoses.

Mood and anxiety disorders, including depression and obsessive-compulsive disease may also be treated with the compounds and compositions according to the invention.

Compounds with modulating effects on dopaminergic systems may also be used to improve cognitive functions and in the treatment of emotional disturbances related to ageing, neurodegenerative (e.g. Dementia and age-related cognitive impairment) and developmental (such as Autism spectrum disorders, ADHD, Cerebral Palsy, Gilles de la Tourette's syndrome) disorders as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, and environmental toxins. The compounds and their pharmaceutical composition are useful for treatment of a condition selected from the group consisting of sleep disorders, sexual disorders, eating disorders, obesitas, and headaches and other pains in conditions characterized by increased muscular tone. They may also be used in the treatment of Alzheimer's disease or related dementia disorders.

The compounds and compositions according to the invention may also be used in behavioural disorders usually first diagnosed in infancy, childhood, or adolescence as well as in impulse control disorders.

They can also be used for treating substance abuse disorders as well as disorders characterized by misuse of food.

Neurological indications include the use of the compounds and their compositions to improve mental and motor function in Parkinson's disease, dyskinesias (including L-DOPA induced dyskinesias), and in related Parkinsonian syndromes. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds according to the invention.

The present invention also relates to the use of a compound of Formula I as shown above wherein R is selected from the group consisting of $C_1$-$C_3$ alkyls and allyl, or a pharmaceutically acceptable salt thereof in the manufacture of pharmaceutically active preparations for the treatment of a disorder of the central nervous system. The disorder of the central nervous system may be one or more of the disorders described above. In particular embodiments of the use, R is selected from the group consisting of n-propyl and ethyl.

The compounds according to the present invention have been shown to display dopaminergic stabilizer profile with improved potency (Table 1). They have effects on biochemical indices in the brain with the characteristic features of dopamine antagonists, e.g. producing increases in concentrations of dopamine metabolites. In rat Example 1 increases 3,4 dihydroxyphenylacetic acid (DOPAC) in striatum to 318% of control at 100 µmol/kg s.c. Example 2 increases DOPAC to 292% at 100 µmol/kg s.c.

The compounds of this invention show no effects on spontaneous locomotion over a wide dose range (1-100 µmol/kg s.c).

In some cases, in particular when the baseline activity is low, they can induce a slight behavioural activation. The behavioural activation is limited, not reaching the profound increases in activity induced by direct or indirect dopaminergic agonists. On the other hand, the preferred substances reduce the increase in activity induced by direct or indirect dopaminergic agonists, i.e. d-amphetamine and congeners (Table 1).

Thus, the compounds of this invention show a dopaminergic stabilizer profile with improved or retained potency (Table 1) compared to compounds of formula I and II. In addition, the specific substitution pattern decreased the potency at inhibiting the HERG channel.

Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as reduced side effects.

The compounds of the present invention have also been shown to display high metabolic stability in rat liver microsomes measured as turnover at 15 minutes (Example 1 5%, Example 2 0%), and high oral bioavailability in rat, exemplified by Example 2 (around 85%).

These compounds are thus suitable for the preparation of orally administered pharmaceuticals. There is no guidance in the prior art how to obtain compounds with this effect on behaviour and dopamine systems in the brain.

Pharmacology

Evidence is available that dopaminergic neurotransmission in the CNS is disturbed in psychiatric and neurological diseases. In many instances, for example in schizophrenia, Parkinson's disease, Huntington's disease, bipolar disorder and in dementia pharmacotherapies based on antagonism or agonism at dopamine receptors are useful, but not optimal. In recent years many efforts have been made in finding novel and selective compounds for dopamine receptor subtypes (D1, D2, D3, D4, D5) with the aim to improve efficacy and reduce side effects.

The present invention offers another principle for novel therapeutics based on interactions with the dopamine system. The invention provides compounds having, as their major feature, stabilizing effects on the dopaminergic system in the brain.

Description of Animal Models Used in the Invention

The compounds according to the invention have effects on brain neurochemistry similar to antagonists at dopamine D2 receptors (i.e. dose-dependent increases of the dopamine metabolite DOPAC, in cortical, striatal and limbic brain regions). The compounds according to the invention show no, or only limited inhibitory, effects on spontaneous locomotion. Under certain conditions they can induce a behavioural activation. The behavioural activation is limited, not reaching the profound increases in activity induced by direct or indirect dopamine receptor agonists. However, the preferred substances reduce the increase in activity induced by the indirect dopaminergic agonist d-amphetamine. The increase in activity after treatment with d-amphetamine is a standard model of hyperdopaminergia (Table 1). In this model, dopaminergic neurotransmission is increased by systemic administration of d-amphetamine at a dose that is sufficiently high to produce a large increase in locomotor activity. The ability of a compound to antagonize this hyperactivity reflects anti-dopaminergic properties, which are part of the dopaminergic stabiliser profile. Furthermore, antagonism of d-amphetamine induced hyperactivity is widely used as a standard assay of antipsychotic activity (see Psychopharmacology 4th Generation of progress Chapter 68, p 793-795).

Another animal model of antipsychotic activity is based on administration of the glutamate antagonist MK-801. Glutamate antagonists (i.e. NMDA antagonists), can induce psychoses in man (see Psychopharmacology, 4th Generation of progress Chapter 101, p. 1205 and 1207) and induce behavioural aberrations in animals. Thus, the ability of a drug to affect schizophrenia and psychotic states can be measured using behavioural models based on experimentally induced hypoglutamatergic states. In this study the NMDA antagonist MK-801 (0.7 mg/kg i.p.) was used to create a hypoglutamatergic state where the rats display abnormal, hyperactive behaviour. Compounds in the present invention dose-dependently reverse the behavioural aberration induced by MK-801 (see Table 2).

It is known that the dopaminergic systems of the brain interacts strongly with other transmitter systems (see Psychopharmacology, 4th Generation of progress, Chapter 101, pages 1208-1209). Such interactions can explain the powerful effects of dopaminergic stabilizers on the behavioural aberrations induced by the glutamate antagonist MK-801 although these aberrations are not primarily based on or caused by changes in dopaminergic transmission.

TABLE 2

Effects of compounds from the present invention on Locomotor activity in MK-801 pre-treated rats (0.7 mg/kg i.p. 90 minutes before test compound). The animals were placed in the motility meters immediately after test compound administration and locomotor activity was recorded between 30 and 60 minutes after administration (counts/30 min ± SEM)

| | Control group | MK-801 0.7 mg/kg i.p. | MK + example 100 μmol/kg |
|---|---|---|---|
| Example 1 | 47 ± 12 | 58630 ± 9344 | 20858 ± 4638 (P = 0.01) |
| Example 2 | 31 ± 9.6 | 58753 ± 10982 | 24012 ± 5511 (P = 0.03) |

Therapeutic Use of Dopaminergic Stabilizers

The claimed invention provides compounds having, as their major feature, stabilizing effects on the dopaminergic system in the brain. These compounds are useful for treating CNS disorders in which the symptoms can be affected by dopaminergic functions. In support of this assertion, please see the following references:

- In support of schizophrenia and psychosis, Applicants refer to Psychopharmacology 4th Generation of progress Chapter 26, p. 295-301);
- Parkinson's disease (Psychopharmacology 4th Generation of progress Chapter 26, p 295, Chapter 1479-1482);
- Anxiety disorders (Psychopharmacology 4th Generation of progress Chapter 21, p. 227 and 237, Chapter 111, p. 1317-1318 and 1320);
- Mood disorders (Psychopharmacology 4th Generation of progress Chapter 80, p. 921-928; and
- Substance abuse (Psychopharmacology 4th Generation of progress Chapter 25, p. 283 and 292, Chapter 66, p. 759-760, Chapter 147, p. 1725 (see also Nisell et al, "Systemic Nicotine-Induced Dopamine Release in the Rat Nucleus Accumbens is Regulated by Nicotinic receptors in the Ventral Tegmental Area; *Synapse* (1994) 16: 36-44). Chapter 149, p. 1745-1747 and 1751-1752). Drugs abused by humans preferentially increase synaptic dopamine concentrations in the mesolimbic system of freely moving rats Di Chiara et al *Proc Natl Acad Sci USA* 85, 5274, 1988. Drug addiction as a disorder of associative learning. Role of nucleus accumbens shell/extended amygdala dopamine *Ann N.Y. Acad Sci* 877, 461, 1999.

As shown by these references, the claimed conditions are recognized in the art as diseases which concern dopaminergic neurotransmission.

Furthermore, pharmacological interaction with dopaminergic neurotransmission is widely believed to be useful in the treatment of several CNS disorders, which are not generally believed to be directly caused by disruptions in dopaminergic neurotransmission. For example, the symptoms of Huntington's disease and other movement disorders can be treated with dopaminergic agents due to the involvement of dopamine in motor functions-(see Psychopharmacology 4th Generation of progress, Chapter 26, p. 295-301). Likewise, it is known that cognitive disorders (see Psychopharmacology 4th Generation of progress Chapters 25, p. 292, Chapter 120, p. 1417 and 1420, Chapter 123, p. 1447 and 1452 and 1455-1457) autism (see Psychopharmacology 4th Generation of progress Chapter 142, p. 1653 and 1661), attention-deficit hyperactivity disorders (see Psychopharmacology 4th Generation of progress Chapter 141, p. 1643 and 1649-1650), sexual disorders (see Psychopharmacology 4th Generation of progress Chapters 65, p. 743-746 and Chapter 22, p. 245 and 254) and eating disorders (see Psychopharmacology 4th Generation of progress Chapters 137, p. 1600, Chapter 138, p. 1609-1610 and 1612) may be treated with agents strengthening dopaminergic transmission. Thus, the above references support the argument that the compounds of the invention would be useful in the treatment of such diseases.

It is widely recognised that inhibition of the HERG channel can induce severe cardiac side-effects, including lethal arrhythmia (J. Cardiovasc. Electrophysiol. 15, 475, 2004; Eur. 3. Pharm., 450, 37, 2002; Cardiovascular Research, 58, 32, 2003). Thus in the development of new CNS pharmaceuticals, compounds with minimal affinity at the HERG channel, leading to a wide safety margin, are sought.

Methods of Preparation

The compounds of the invention may be prepared as outlined below in Scheme 1. However, the invention is not limited to these methods. The compounds may also be prepared as described for structurally related compounds in the prior art. The reactions can be carried out according to standard procedures[1,2] or as described in the working examples. The starting materials for the processes described in the present application are known or may readily be prepared by conventional methods from commercially available chemicals.

Persons skilled in the art will appreciate that, in order to obtain compounds of the invention in an alternative and in some occasions, more convenient manner, the individual process steps mentioned hereinbefore may be performed in a different order, and/or the individual reactions may be performed at a different stage in the overall route (i.e. chemical transformations may be performed upon different intermediates to those associated hereinbefore with a particular reaction).

Scheme 1

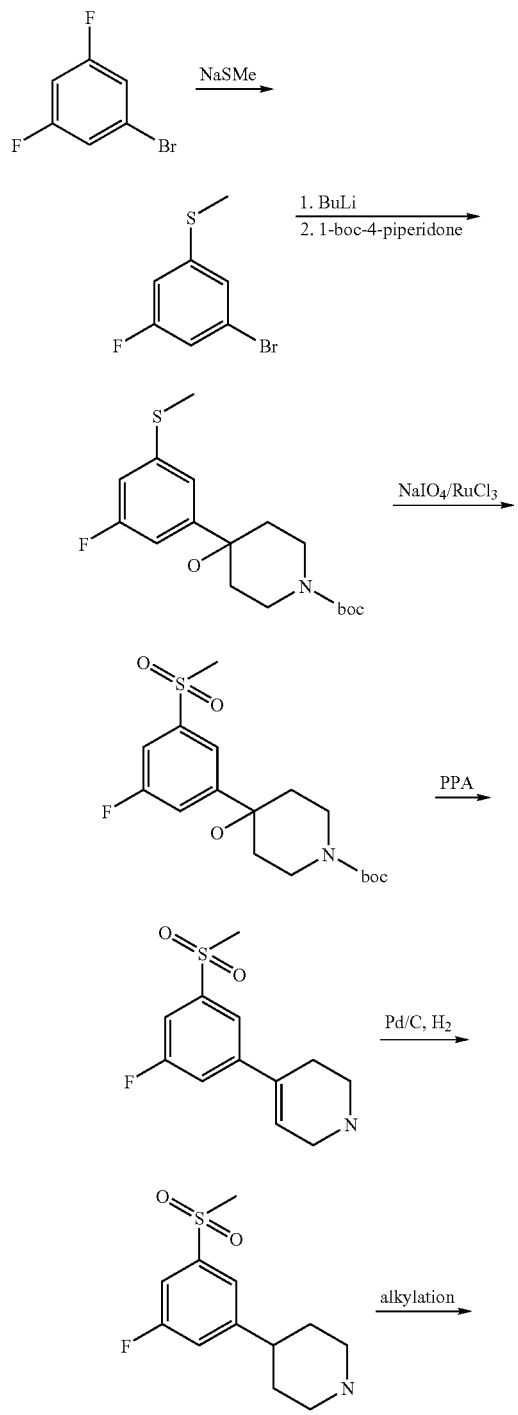

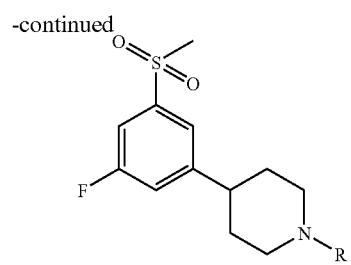

Ref.
1. Comprehensive Organic Transformations: A Guide to Functional Group Preparations
   Richard C. Larock, 22 Oct., 1999 Wiley-VCH
   ISBN: 0471190314
2. March's Advanced Organic Chemistry: Reactions, Mechanisms, and Structure, 5th Edition.
   Michael B. Smith, Jerry March, Jan. 15, 2001 Wiley-Interscience
   ISBN: 0471585890

As used herein the term $C_1$-$C_3$ alkyl refers to an alkyl containing 1-3 carbon atoms in any isomeric form. The various carbon moieties are defined as follows: Alkyl refers to an aliphatic hydrocarbon radical and includes unbranched forms such as methyl, ethyl, n-propyl, The term "allyl" refers to the group —$CH_2$—CH=$CH_2$.

The term "patient" used herein refers to an individual in need of the treatment according to the invention.

The term "treatment" used herein relates to both treatment in order to cure or alleviate a disease or a condition and to treatment in order to prevent the development of a disease or a condition. The treatment may either be performed in an acute or in a chronic way.

Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as toluensulfonate, methanesulfonate, fumarate, hydrochloride, hydrobromide, hydroiodide, nitrate, acetate, lactate, citrate, acid citrate, tartrate, bitartrate, aliphatic, alicyclic, aromatic or heterocyclic carboxylate, succinate, maleate, fumarate, gluconate, glycolate, saccharate, ascorbate, acetate, propionate, benzoate, pyruvate, pamoate [i.e., 1,1'-methylene-bis-(2-hydroxy-3-naphthoate)], phosphate, acid phosphate, sulphate or bisulfate salts. These salts are readily prepared by methods known in the art. It is also to be understood that compounds of the present invention can exist in solvated as well as unsolvated forms such as, e.g, hydrated forms.

The pharmaceutical composition containing a compound according to the invention may also comprise substances used to facilitate the production of the pharmaceutical preparation or the administration of the preparations. Such substances are well known to people skilled in the art and may for example be pharmaceutically acceptable adjuvants, carriers and preservatives.

In clinical practice the compounds used according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier.

The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules. Examples of tablet and capsule formulations suitable for oral administration are given below:

|  | mg/tablet |
|---|---|
| Tablet I | |
| Compound | 100 |
| Lactose Ph.Eur | 182.75 |
| Croscarmellose sodium | 12.0 |
| Maize starch paste (50% w/v paste) | 2.25 |
| Magnesium stearate | 3.0 |
| Tablet II | |
| Compound | 50 |
| Lactose Ph.Eur | 223.75 |
| Croscarmellose sodium | 6.0 |
| Maize starch | 15.0 |
| Polyvinylpyrrolidone (50% w/v paste) | 2.25 |
| Magnesium stearate | 3.0 |
| Tablet III | |
| Compound | 1.0 |
| Lactose Ph.Eur | 93.25 |
| Croscarmellose sodium | 4.0 |
| Maize starch paste (50% w/v paste) | 0.75 |
| Magnesium stearate | 1.0 |

| Capsule | mg/capsule |
|---|---|
| Compound | 10 |
| Lactose Ph.Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated in the clinic would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas.

The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve which delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 μM of the compound is obtained.

Any chemical formula or name given herein is meant to include all stereo and optical isomers and racemates and mixtures thereof in any ratio. The various isomers can be obtained by standard methods well known to persons skilled in the art, e.g. via chromatography or fractional crystallisation. For example, cis/trans mixtures can be separated into the individual stereoisomers by stereoselective synthesis. Enantiomers or diastereomers may be isolated by separation of their mixtures, for instance by fractional crystallisation, resolution or HPLC. Alternatively separation can be afforded by derivatisation with a chiral reagent. Stereoisomers may be made by stereoselective synthesis from stereochemically pure starting materials under conditions which will not cause loss of stereochemical integrity. All stereoisomers are included within the scope of the invention.

The compounds of the present invention may be isolated in any level of purity by standard methods and purification can be achieved by conventional means known to those skilled in the art, such as distillation, recrystallization and chromatography.

The invention is further illustrated in the examples below, which in no way are intended to limit the scope of the invention.

EXAMPLE 1

4-[3-fluoro-5-(methylsulfonyl)phenyl]-1-propylpiperidine

To a solution of 4-[3-fluoro-5-(methylsulfonyl)phenyl]piperidine (0.5 g, 1.94 mmol) in acetonitrile (5 ml) was added potassium carbonate (0.53 g, 3.83 mmol) and 1-iodopropane (0.189 ml, 1.94 mmol) and the mixture was heated with microwave irradiation for 20 min at 150° C. The mixture was cooled to ambient temperature and water (50 ml) was added. The aqueous residue was extracted with ethylacetate (3×50 ml) and the combined organic phases was dried, concentrated, and purified by flash column chromatography (ethylacetate/methanol, 1:1) to give the title compound (0.27 g, 46%). The amine was converted to the hydrochloric acid salt and recrystallized from ethanol/diethyl ether: M.p. 187-189° C. MS m/z (relative intensity, 70 eV) 299 (M+, 3), 271 (15), 270 (bp), 147 (5) 133 (5).

EXAMPLE 2

1-ethyl-4-[3-fluoro-5-(methylsulfonyl)phenyl]piperidine

Preparation according to Example 1: 4-[3-fluoro-5-(methylsulfonyl)phenyl]piperidine (0.4 g, 1.55 mmol), acetonitrile (5 ml), potassium carbonate (0.42 g, 3.0 mmol), 1-iodoethane (0.147 ml, 1.55 mmol). Yield: 0.28 g (63%). The amine was converted to the hydrochloric acid salt and recrystallized from ethanol/diethyl ether: M.p. 176-178° C. MS m/z (relative intensity, 70 eV) 285 (M+, 15), 284 (16), 271 (16), 270 (bp), 84 (15).

Synthesis of Intermediates Used in the Above Examples are Described in the Preparations Below.

Preparation 1

1-bromo-3-fluoro-5-(methylthio)benzene

To a solution of 1-bromo-3,5-difluorobenzene (5.0 g, 25.9 mmol) in dimethylformamide (40 ml) was added sodiumthiomethylate (1.81 g, 25.9 mmol), and the mixture was heated to 150° C. for 10 min. The reaction mixture was brought to ambient temperature, quenched with saturated aqueous ammonium chloride (100 ml) and extracted with ethylacetate (3×100 ml). The combined organic phases was dried and concentrated in vacuo to receive the pure title compound (3.84 g). MS m/z (rel. intensity, 70 eV) 222 (M+, 100), 220 (M+, 100), 189 (49), 187 (50), 126 (75).

Preparation 2 tert-butyl 4-[3-fluoro-5-(methylthio)phenyl]-4-hydroxypiperidine-1-carboxylate

To a solution of 1-bromo-3-fluoro-5-(methylthio)benzene (3.7 g, 16.7 mmol) in dry diethylether (100 ml), under nitrogen, at −78° C. was added dropwise n-butyl lithium (2.5 M in hexane, 6.7 ml, 16.7 mmol). The mixture was stirred for 30 min at −78° C. and then brought to −20° C. for 2 min and cooled again to −78° C. To the resulting mixture at −78° C., a solution of 4-Boc-1-piperidone (3.3 g, 16.7 mmol) in dry diethylether (50 ml) was added drop wise. The mixture was stirred at −78° C. for 10 min and then brought to ambient temperature. The reaction mixture was quenched with saturated aqueous ammonium chloride (100 ml) and extracted with ethylacetate (3×100 ml). The combined organic phases was dried, concentrated, and purified by flash column chromatography (isooctane/ethylacetate 2:1) to give the title compound (3.76 g). MS m/z (rel. intensity, 70 eV) 341 (M+, 7), 285 (11), 241 (11), 196 (4), 57 (bp).

Preparation 3 tert-butyl-4-[3-fluoro-5-(methylsulfonyl)phenyl]-4-hydroxypiperidine-1-carboxylate To a solution of tert-butyl 4-[3-fluoro-5-(methylthio)phenyl]-4-hydroxypiperidine-1-carb-oxylate (3.66 g, 10.6 mmol) in carbontetrachloride (13 ml), acetonitrile (13 ml) and water (26 ml), was added sodium periodate (6.8 g, 31.8 mmol) and ruthenium trichloride (3 mg, 0.05 mol %) and the mixture was stirred for 20 min. at ambient temperature. Water was added and the product was extracted with ethylacetate (3×100 ml). The combined organic phases was dried and concentrated in vacuo to receive the pure title compound (3.3 g). MS m/z (rel. intensity, 70 eV) 373 (M+, 0), 273 (25), 255 (74), 133 (28), 56 (bp).

Preparation 4

4-[3-fluoro-5-(methylsulfonyl)phenyl]-1,2,3,6-tetrahydropyridine

A mixture of tert-butyl 4-[3-fluoro-5-(methylsulfonyl)phenyl]-4-hydroxypiperidine-1-carboxylate (3.3 g, 8.8 mmol) and polyphosphoric acid (20 ml) was heated at 120° C. for 3 h. The mixture was poured on to ice and was basified with 5 M sodium hydroxide. The mixture was extracted with ethylacetate (3×100 ml) and the combined organic phases was dried (MgSO$_4$), evaporated and purified by flash column chromatography (methanol/ethylacetate 1:1) to give the title compound (2.02 g). MS m/z (rel. intensity, 70 eV) 255 (M+, bp), 254 (50), 251 (87), 172 (87), 146 (53).

Preparation 5

4-[3-fluoro-5-(methylsulfonyl)phenyl]piperidine

A mixture of 4-[3-fluoro-5-(methylsulfonyl)phenyl]-1,2,3,6-tetrahydropyridine (2.02 g, 7.9 mmol), palladium on carbon (0.56 g) and formic acid (1.9 ml) in isopropyl alcohol (60 ml) was hydrogenated at 50 psi for 24 h under hydrogen. The reaction mixture was filtered through a pad of celite and the filtrate was concentrated and evaporated to dryness to give 1.66 g of crude product. MS m/z (relative intensity, 70 eV) 257 (M+, bp), 256 (80), 133 (21), 69 (25) 56 (99).

The following tests were used for evaluation of the compounds according to the invention.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and a Apple Macintosh computer equipped with a digital interface board (NB DIO-24, National Instruments, USA). Each activity monitor consisted of a quadratic metal frame (W×L 40×40 cm) equipped with photobeam sensors. During measurements of behavioural activity, a rat was put in a transparent acrylic cage (W×L×H, 40×40×30 cm) which in turn was placed in the activity monitor. Each activity monitor was equipped with three rows of infrared photobeam sensors, each row consisting of 16 sensors. Two rows were placed along the front and the side of the floor of the cage, at a 90° angle, and the third row was placed 10 cm above the floor to measure vertical activity. Photobeam sensors were spaced 2.5 cm apart. Each activity monitor was fitted in an identical sound and light attenuating box containing a weak house light and a fan.

The computer software was written using object oriented programming (LabVIEW®, National instruments, Austin, Tex., USA).

Behavioural data from each activity monitor, representing the position (horizontal centre of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 4 min after the injection of test compound. Similar behavioural recording procedures were applied for drug-naïve and drug pre-treated rats. Rats pretreated with d-amphetamine were given a dose of 1.5 mg/kg i.p. 10 min before the recording session in the activity monitor. Rats pretreated with MK-801 were given a dose of 0.7 mg/kg i.p. 90 min before the recording session in the activity monitor. The results are presented as counts/60 minutes, or counts/30 minutes, in arbitrary length units. Statistical comparisons were carried out using student's t-test vs the control group. In MK-801 or amphetamine pre-treated animals, statistical comparisons were made vs the MK801 or d-amphetamine controls, respectively.

$ED_{50}$ values for reduction of amphetamine-induced hyperlocomotion are calculated by curve fitting. For most compounds, the evaluation is based on 16 amphetamine pre-treated animals over the dose range 0, 11, 33 and 100 µmol/kg s.c. in one single experiment, with complementary doses in separate experiments. Calculations are based on distance during the last 45 minutes of one hour of measurement. The distances are normalized to amphetamine-control and fitted by least square minimization to the function "End-(End-Control)/(1+(dose/$ED_{50}$)$^{Slope}$)". The four parameters are fitted with the restrictions: $ED_{50}$>0, 0.5<Slope<3, End>0% of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Neurochemistry

After the behavioural activity sessions, the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3µ, 50*2 mm i.d., Phenomenex) and electrochemical detection is accomplished at two potentials on glassy carbon electrodes (MF-1000, Bioanalytical Systems, Inc.). Via a T-connection the column effluent is passed to the detection cell or to waste. This is accomplished by two solenoid valves, which block either the waste or detector outlet. By not letting the chromatographic front reach the detector, better detection conditions are achieved. The aqueous mobile phase (0.4 ml/min) for the acid system contains Citric Acid 14 mM, Sodium Citrate 10 mM, MeOH 15% (v/v) and EDTA 0.1 mM. Detection potentials relative to Ag/AgCl reference is 0.45 and 0.60V. The aqueous ion pairing mobile phase (0.5 ml/min) for the amine system contains Citric Acid 5 mM, Sodium Citrate 10 mM, MeOH 9% (v/v), MeCN 10.5% (v/v), Decane Sulfonic Acid 0.45 mM, and EDTA 0.1 mM. Detection potentials relative to Ag/AgCl reference is 0.45 and 0.65V.

In Vivo Test: Oral bioavailability

Experiments are performed 24 hours after implantation of arterial and venous catheters. Test compound is administered orally at 12.5 µmol/kg or intravenously at 5 µmol/kg using the venous catheters, n=3 per group. Arterial blood samples are then taken during eight hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following: AUC: the area under the plasma concentration versus time curve from time zero to the last concentration measured (Clast), calculated by the log/linear trapezoidal method.

The levels of test compound are measured by means of liquid chromatography-mass spectrometry (LC-MS). (Hewlett-Packard 1100MSD Series). The module include a quaternary pump system, vacuum degasser, thermostatted autosampler, thermostatted column compartment, diode array detector and API-ES spray chamber. Data handling was performed with a HP ChemStation rev.A.06.03. system. Instrument settings:MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 µm) at 20° C. The mobile phase was acetic acid (0.03%) (solvent A) and acetonitrile (solvent B). The flow rate of the mobile phase was 0.8 ml/min. The elution was starting at 12% of solvent B isocratic for 4.5 min, then increasing linearly to 60% over 4.5 min.

Extractions procedure: Plasma samples (0.25-0.5 ml) were diluted with water to 1 ml, and 60 pmol (100 µl) internal standard (−)-OSU6241 was added. The pH was adjusted to 11 by the addition of 25 µl saturated aqueous sodium carbonate. After mixing, the samples were extracted with 4 ml dichloromethane by shaking for 20 min. The organic layer was after centrifugation transferred to a smaller tube and evaporated to dryness under a stream of nitrogen. The residue was then dissolved in 120 µl mobile phase (acetic acid (0.03%):acetonitrile, 95:5) for LC-MS analysis (10 µl injected). The selective ion ($MH^+$) was monitored for each Example, and $MH^+$ 296 for (−)-OSU6241 ((3-[3-(ethylsulfonyl)phenyl]-1-propylpiperidine).

A standard curve over the range of 1-500 pmol is prepared by adding appropriate amounts of test compound to blank plasma samples.

In Vitro Test: Metabolic Stability in Rat Liver Microsomes

Rat liver microsomes were isolated as described by Forlin (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo garirdneri, of different age and sex. Tox Appl Pharm. 54(3) 420-430, with minor modifications e.g. 3 mL/g liver of a 0.1 M $Na/K*PO_4$ buffer with 0.15 M KCl, pH 7.4, (buffer 1) was added before homogenisation, the homogenate was centrifuged for 20 minutes instead of 15, the supernatant was ultracentrifuged at 100.000 g instead of 105.000 g and the pellet from the ultracentrifugation was re-suspended in 1 mL/g liver of 20% v/v 87% glycerol in buffer 1.

1 µL of, 0.2 or 1 mM test substance diluted in water and 10 µL 20 mg/mL rat liver micro-some were mixed with 149 µL 37° C. buffer 1 and the reaction was started by addition of 40 µL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction was stopped by addition of 100 µL pure acetonitrile. The protein precipitation was then removed by rejecting the pellet after centrifugation at 10.000 g for 10 minutes (Heraeus, Biofuge fresco) in 4° C. The test compound was analysed using HPLC-MS (Hewlett-Packard 1100MSD Series) with a Zorbax SB-C18 column (2.1*150 mm, 5 µm) using 0.03% formic acid and acetonitrile as mobile phase (gradient) or a Zorbax Eclipse XDB-C18 (3*75 mm, 3.5 µm) using 0.03% acetic acid and acetonitrile as mobile phase (gradient). The 15 min turnover was calculated as the fraction of test compound eliminated after 15 minutes, expressed in percent of 0 min levels, ie 100*[conc test compound at 0 min−concentration at 15 min]/conc at 0 min.

Preparation of liver microsomes was performed as described in Forlin (1980). Protocols for incubation with liver microsomes are provided in Crespi & Stresser (2000), and Renwick et al (2001).

Crespi C L, and D M Stressser (2000). Fluorometric screening for metabolism based drug-drug interactions. J. Pharm. Tox. Meth. 44. 325-331

Förlin L. (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. Tox Appl Pharm. 54(3) 420-430

Renwick, A B et al. (2001). Metabolism of 2,5-bis(trifluoromethyl)-7-benzyloxy-4-trifluoromethylcoumarin by human hepatic CYP isoforms: evidence for selectivity towards CYP3A4. Xenobiotica 31(4): 187-204 hERG Affinity

Assessment of hERG affinity by rapid ICE™ was performed by Quintiles Limited, Research Avenue South, Heriot-Watt University Research Park, Riccarton Edinburgh, Scotland. Rapid ICE™ (Rapid Ion Channel Electrophysiology) is an automated patch-clamp assay utilising the PatchXpress 7000A system (Axon Instruments). Rapid ICE™ assesses the effect of test substances on HERG tail current recorded from HEK293 cells stably transfected with HERG cDNA. Compounds that inhibit HERG current have been shown to prolong the cardiac action potential and hence QT interval in man.

HERG.T.HEK (HEK293 cells stably transfected with HERG cDNA) were obtained from the University of Wisconsin. These cells are held in cryogenic storage at Quintiles and also maintained in culture. The cells are continuously maintained in and passaged using minimum essential medium supplemented with 10% foetal bovine serum, 1% non-essential amino acids, 1% sodium pyruvate and 0.4 mg/ml geneticin. For use in Rapid ICE™ studies, 4 ml of the cells are placed into falcon tubes at a density of 2.5×10 5/ml. The falcon tubes are stored in a humidified, gassed (5% $CO_2$) incubator at 37° C. and cells are used within 2.5 h of storage. Just prior to experimentation, these cells are centrifuged at 1000 rpm for 1 min, the supernatant decanted and the cells re-suspended in 150 µl of bath solution in a 1.5 ml eppendorf tube.

The PatchXpress system is primed with appropriate extracellular (bath) and intracellular (pipette) solutions prior to conducting a study. A 16 well sealchip (Sealchip16, Aviva Bio-sciences Corp) is loaded into the system and primed before preparing cells in the bath solution suspension. The cell eppendorf is placed into the designated position and the procedure commences with the trituration and dispersion of cells into each well (recording chamber) of the sealchip. The PatchXpress system follows the general principles of conventional whole-cell patch-clamping: a high resistance seal is formed between the patch electrode and an individual cell, the membrane across the electrode tip is ruptured and the whole-cell patch-clamp configuration is established. If the quality of the cell is judged to be poor, the experiment may be terminated at this point and if necessary, the process repeated on another sealchip.

Once a stable patch has been achieved, recording commences in voltage-clamp mode, with the cell initially clamped at −80 mV. The standard voltage profile is as follows: step from −80 mV to −50 mV for 200 ms, +20 mV for 4.8 s, step to −50 mV for 5 s then step to the holding potential of −80 mV. The step from −80 mV to the test command (+20 mV) results in an outward current (i.e. current flows out of the cell) and the step from the test command (+20 mV) to −50 mV results in the tail current (the tail current represents deactivation of the current over time). Tail current values are extracted. Each value represents the average current recorded from 4 sequential voltage pulses. For each cell the effects of the test substance is determined by calculating the residual current (% control) compared with vehicle pre-treatment.

An IC50 value (µM), or other marker of potency, is estimated from the concentration-response relationship.

The invention claimed is:
1. A phenyl-piperidine compound which is
1-ethyl-4-[3-fluoro-5-(methylsulfonyl)phenyl]piperidine;
or a pharmaceutically acceptable salt thereof.

2. A phenyl-piperidine compound according to claim 1, which is the hydrochloride salt of 1-ethyl-4-[3-fluoro-5-(methylsulfonyl)phenyl]piperidine.

\* \* \* \* \*